United States Patent
Maor et al.

(10) Patent No.: US 6,582,709 B1
(45) Date of Patent: Jun. 24, 2003

(54) CREAM COMPOSITION COMPRISING DEAD SEA MUD

(75) Inventors: Zeev Maor, Dead Sea (IL); Shaul Yehuda, Dead Sea (IL); Shlomo Magdassi, Jerusalem (IL); Galit Meshulam-Simon, Tivon (IL); Yona Gavrieli, Tivon (IL); Zivn Gilad, Dead Sea (IL); Dov Efron, Jerusalem (IL)

(73) Assignee: Dead Sea Laboratories Ltd., Dead Sea (IL)

( * ) Notice: Subject to any disclaimer, the term of this patent is extended or adjusted under 35 U.S.C. 154(b) by 0 days.

(21) Appl. No.: 09/869,827

(22) PCT Filed: Jan. 6, 2000

(86) PCT No.: PCT/IL00/00011

§ 371 (c)(1),
(2), (4) Date: Oct. 15, 2001

(87) PCT Pub. No.: WO00/40255

PCT Pub. Date: Jul. 13, 2000

(30) Foreign Application Priority Data

Jan. 7, 1999 (IL) .................................. 127943

(51) Int. Cl.⁷ ............................ A61K 7/00; A61K 33/00
(52) U.S. Cl. ........................ 424/401; 424/600; 514/844; 514/847; 514/861; 514/863; 514/864; 514/865; 514/938
(58) Field of Search ................................. 424/401, 600; 514/844, 847, 861, 863, 864, 865, 938

(56) References Cited

U.S. PATENT DOCUMENTS

| | | | | |
|---|---|---|---|---|
| 5,679,378 A | * | 10/1997 | Fischer | 424/600 |
| 5,705,172 A | * | 1/1998 | Efron et al. | 424/402 |
| 6,139,553 A | * | 10/2000 | Dotan | 601/70 |
| 6,162,458 A | * | 12/2000 | Asada et al. | 424/195.15 |

FOREIGN PATENT DOCUMENTS

| | | | |
|---|---|---|---|
| DE | 32 21 502 A | | 12/1983 |
| GB | 2 253 143 A | * | 2/1992 |
| JP | 09 175955 A | | 9/1997 |
| WO | 97 22348 A | | 6/1997 |

* cited by examiner

*Primary Examiner*—Jose' G. Dees
*Assistant Examiner*—Marina Lamm
(74) *Attorney, Agent, or Firm*—Lowe Hauptman Gilman & Berner, LLP

(57) ABSTRACT

The preset invention relates to a pharmaceutical cream composition for topical application for the treatment of skin disorders and skin diseases, comprising 1–6 wt. % Dead Sea Mud as an active ingredient. Said composition is for use in treating skin disorders and skin diseases such as psoriasis, saborrehic dermatitis, xerosis, attopic dermatitis, eczema, diaper rush, skin burns of stage I and sensitive skin. Said cream composition is also for use as a leave-on cosmetic cream for beautifying and enhancing the skin appearance. In addition to Dead Sea Mud said composition comprises ingredients suitable for the preparation of cosmetic cream. Said cream can further comprises up to 4 wt % Dead Sea water.

13 Claims, No Drawings

CREAM COMPOSITION COMPRISING DEAD SEA MUD

FIELD OF THE INVENTION

The present invention relates to pharmaceutical and cosmetic cream compositions containing Dead Sea Mud for topical skin application. More specifically, the present invention relates to compositions for prevention and treatment of skin related disorders such as saborrehic dermatitis, xerosis, eczema, psoriasis and skin burns and for cosmetic use for retaining skin moisture and repairing of impaired skin.

BACKGROUND OF THE INVENTION

The skin is the largest organ in the body, serving as a protective barrier from the external environment. As such it is susceptible to various disorders and diseases caused by microorganisms, exposure to radiation, contact with irritating materials and loss of water.

Dead Sea mud and water are known for their therapeutic and cosmetic properties (for example see Ma'or Z. and Yehuda S. (1997) *International Journal of Cosmetic Science* 19: 105–110). Various cosmetic products based on these properties exist in the market. For example, Japanese application JP 96011775 discloses a beauty plaster, comprising among other ingredients, natural salt and mud from the Dead Sea. PCT application No. PCT/IL98/00311 (applicant: Dead Sea Laboratories Ltd.) discloses a composition for skin care and protection comprising 10–15% of Dead Sea water.

Dead Sea mud is especially known for its therapeutic properties on psoriasis and other skin related disorders. Patients, suffering from various skin diseases come to the Dead Sea to have treatments with Dead Sea Mud, often upon their physician recommendation.

However, treatment with raw Dead Sea Mud has several drawbacks. It may be quite expensive and inconvenient for patients to travel to the Dead Sea for receiving treatment. The other possibility, delivering raw mud to the patient's home, is inconvenient due to the large amounts that must be applied for each treatment (10 Kg). Furthermore, the treatment with Dead Sea mud is quite messy and is limited to short time periods, since the mud cannot be left on the body for long periods of time due to inconvenience and aesthetic reasons.

It is the aim of the present invention to overcome the problems associated with treatments with Dead Sea water by providing an easy and pleasant to use creams that while having the therapeutic benefits of the Dead Sea mud do not suffer from the above mentioned disadvantages.

The incorporation of mud (in our case, Dead Sea mud) into a leave-on cream which should be evenly spreadable, aesthetic (i.e., unnoticeable), pleasant to use and absorbed easily to the skin, is not simple, because it involves a suspension of solid particles in an oil-in-water emulsion that contains electrolytes in a very high concentration. Such a combination has a high tendency to aggregate and to separate into phases. Still the cream must be stable and with a reasonable shelf life.

The present invention overcomes said difficulties by proper selection of stabilizers and other components, and provides a cream that has the benefits of treatment with Dead Sea mud, but non of the drawbacks. It is an easy and simple to use hypoallergenic cream that is absorbed into the skin and in contrast to the treatments used today, it may be in prolonged contact with the skin (i.e., leave-on cream), enhancing the beneficial effects of the Dead Sea mud. It is also stable, does not separate to phases, and has long shelf life.

In the context of the present invention the term "cosmetic cream" relates to an oil-in-water emulsion, suitable for applying to skin, of various viscosity ranges including milk, lotion, cream and ointment.

The term "pharmaceutical cream" relates to an oil-in-water emulsion of various viscosity including milk, lotion, cream and ointment for the use of treating (healing) and preventing or delaying skin disorders and diseases.

The term "leave on cream" (in contrary to "rinse off") relates to a cream that may be in prolonged contact with the skin and can be applied to the skin without the need to wipe it off in any way.

SUMMARY OF THE INVENTION

The present invention relates to a pharmaceutical cream composition for topical application for the treatment of skin disorders and skin diseases, comprising 1–6 wt. % Dead Sea Mud as an active ingredient. Said composition is for use in treating skin disorders and skin diseases such as psoriasis, saborrehic dermatitis, xerosis, attopic dermatitis, eczema, diaper rush, skin burns of stage I and sensitive skin.

Said cream composition is also for use as a leave-on cosmetic cream for beautifying and enhancing the skin appearance.

In addition to Dead Sea Mud said composition comprises ingredients suitable for the preparation of cosmetic cream.

In a preferred embodiment, said ingredients are selected from Octyl Palmitate, Cetearyl Alcohol, Ceteareth-30, Hexadeacanol, Glyceryl Stearate, Glycerin, PEG-40 Stearate, Zinc Oxide, Propylene Glycol, Aloe Barbadensis Extract, Dimethicone, Sorbitan Tristearate, Allantoin, Methylparaben, Propylparben, Vitamin E (Tocopherol), Bronopol.

Said cream can further comprises up to 4 wt % Dead Sea water.

The present compositions can further contain a fragrance.

DETAILED DESCRIPTION OF THE INVENTION

The present invention relates to pharmaceutical cream composition for topical application for the treatment of skin disorders and skin diseases, comprising 1–6 wt. % Dead Sea Mud as an active ingredient. Said composition is also for use as a cosmetic leave-on composition for beautifying and enhancing the skin appearance.

Said composition is prepared by adding 1–6 wt. % Dead Sea Mud and optionally up to 4% Dead Sea water to cosmetic oil-in-water emulsion comprising of ingredients suitable for the preparation of a cosmetic cream such as ingredients selected from Octyl Palmitate, Cetearyl Alcohol (and) Ceteareth-30, Hexadeacanol, Glyceryl Stearate, Glycerin, PEG-40 Stearate, Zinc Oxide, Propylene Glycol (and) Aloe Barbadensis Extract, Dimethicone, Sorbitan Tristearate, Allontoin, Methylparaben, Propylparben, Vitamin E (Tocopherol), Bronopol and fragrance.

The present composition was found to be efficient in the treatment of the following skin disorders and diseases: Psoriasis, Saborrehic dermatitis, Xerosis (very dry skin), Attopic dermatitis, Eczema, Diaper rush, sensitive skin, and skin burns of stage I.

Dead Sea Mud (Silt) as defined in the present invention is (at 25° C.) stable black paste solid with specific density of 1.6–1.8 g/ml, pH=6.4–7.6, Water content of 30–40 %/w and less than 100 cfu/gr and non-pathogenic microbes. The chemical identity of Dead Sea mud is natural sediment, mixture of solid mineral clays with interstitial solution of inorganic salts and sulfide compounds originated from microbiological activity, with particle size 86–98% <0.005 mm, 2–9% 0.005–0.02 mm, 0–7% >0.02 mm.

The major constituents of the Dead Sea Mud are:

The solid phase which is 60–70% of the total weight consists of:
    Water soluble: Halite (20–40%)
    HCl soluble: Carbonates (30–40%): calcite, dolomite, aragonite
    Non HCl-Soluble matter: Silicates (30–40%): quarts, montmorollonite, feldspar, kaolonite In the liquid phase (30–40% dissolved as ions in water):
    chloride ($Cl^-$) 148–190 g/l
    sodium ($Na^+$) 22–32 g/l
    magnesium ($Mg^{2+}$) 30–40 g/l
    calcium ($Ca^{2+}$) 10–15 g/l
    potassium ($K^+$) 6–8 g/l Dead Sea Water, as defined in the present invention, comprises a clear colorless viscous liquid (at 25° C.) with a specific density of 1.2–1.36 g/ml, pH=4.5–5.5 (at 25° C.), less than 100 cfu/gr and non pathogenic microbes.

The major constituents of the Dead Sea Water are:

| | |
|---|---|
| Calcium ($Ca^{-2}$) | 36000–40000 mg/l |
| Chloride ($Cl^-$) | 320000–370000 mg/l |
| Magnesium ($Mg^{+2}$) | 90000–95000 mg/l |
| Potassium ($K^+$) | 1300–1500 mg/l |
| Sodium ($Na^+$) | 1500–2500 mg/l |
| Bromide ($Br^-$) | 11000–12000 mg/l |
| Strontium ($Sr^{-2}$) | 750–850 mg/l |

The preparation of creams according to the present invention involves the facilitation of non-ionic emulsifiers such as ethoxilated sorbitan esters, sorbitan esters, ethoxilated alcohols or fatty acids, alkyl glucosides, mono- and di-glycerides etc.

A preferred embodiment of a cream composition according to the present invention is given in the following Table 1.

Table 1. Raw Ingredients List of preferred embodiment of the present invention:

TABLE 1

Raw Ingredients List of preferred embodiment of the present invention:

| No. | INCI & COLIPA Name and Ingredients | Authority* | Page No. | Quantity |
|---|---|---|---|---|
| 1 | Water (Aqua) | CTFA 95 | 1065 | Up to 100% |
| 2 | Octyl Palmitate | " | 642 | 8.0% |
| 3 | Cetearyl Alcohol (and) Ceteareth-30 | " | 1372 | 5.0% |
| 4 | Hexadeacanol | " | 164 | 4.0% |
| 5 | Glyceryl Stearate | " | 413 | 3.0% |
| 6 | Glycerin | " | 402 | 3.0% |
| 7 | Dead Sea Mud (silt) | " | 912 | 2.0% |
| 8 | Dead Sea Water (Maris Sai Aqua) | " | 1240 | 1.0% |
| 9 | PEG-40 Stearate | " | 734 | 1.0% |
| 10 | Zinc Oxide | " | 1103 | 1.0% |
| 11 | Propylene Glycol (and) Aloe Barbadensis Extract | " | 1330 | 1.0% |
| 12 | Dimethicone | " | 315 | 0.5% |
| 13 | Fragrance (Parfum) | — | — | 0.5% |
| 14 | Sorbitan Tristearate | CFTA 95 | 969 | 0.4% |
| 15 | Allantoin | " | 27 | 0.2% |
| 16 | Methylparaben | " | 589 | 0.2% |
| 17 | Propylparben | " | 859 | 0.2% |
| 18 | Vitamin E (Tocopherol) | " | 1029 | 0.05% |
| 19 | Bronopol | " | 108 | 0.04% |

*CFTA-Cosmetic Fragrance and Toiletries Association nomenclature.

The preparation of the cream composition of the present invention is preferably done by the following steps:

1) Preparing an aqueous phase comprising distilled water, allanotin, methyl paraben, PEG-40 sterarate and glycerin by mixing said components and heating to 75° C.
2) Preparing a lipophilic phase comprising octyl palmitate, cetearyl alcohol, ceteareth-30, hexadeacanol, glyceryl stearate, zinc oxide, propylene glycol, dimethicone, sorbitan tristearate, propylparben, and vitamin E (tocopherol), by mixing at 75° C.
3) Introducing the lipophilic phase dropwise into a reactor containing the aqueous phase (the distance between the rotor and the stator is adjusted to 4 mm) while stirring at 30 rpm and homogenizing the mixture at 1500 rpm.
4) Cooling said mixture obtained in step 3 slowly and adding following components at following temperatures through homogenization,
5) Adding bronopol dissolved in water at 60° C.
6) Adding the fragrance at 45° C.
7) Adding Aloe Barbadensis extract at 35° C.
8) Adding Dead Sea Mud and Dead Sea Water at 25° C.
9) Removing from the reactor to suitable containers.

The composition so obtained is a gray light cream with ingredients concentrations as specified in Table 1 and with the following properties:

Density: 1.00±0.1 g/ml; Viscosity as determined by Brookfield viscometer with needle c: 108,600 cps at 5 rpm and 190,400 cps at 2.5 rpm; pH: 7.0±0.5 and less than 100 cfu/gr. The cream is stable and does not separate into phases and has a shelf life of 3 years.

The present invention will be further illustrated by the following experiments. These experiments do not intend to limit the scope of the invention, but to demonstrate and clarify it only.

EXPERIMENTAL

In a comparative study, the efficiency of the preferred embodiment of the present invention as disclosed in Table 1 was tested for the treatment of facial Seborrehic Dermatitis and for Xerosis.

Experiment 1: Safety clinical tests for hypoallergenecity (according to US Repeat Insult Patch Test, Federal Register. vol. 46, no. 17 Sep. 27, 1978)

The composition of Table 1 was tested for allergenic symptoms on a group of 50 volunteers. The test was performed as follows:

Every 48 hours the composition was spread on the back of each volunteer and was left for 24 hours. This was repeated 9 times.

No one of the group showed allergenic symptoms or irritations signs.

Experiment 2: The efficiency of the preferred embodiment of Table 1 for the treatment of facial Seborrehic Dermatitis.

In a comparative study, the efficiency of the preferred embodiment of the present invention, specified in Table 1, was tested for the treatment of facial Seborrehic Dermatitis.

A group of 15 people with various degrees of illness severity were selected by an expert dermatologist from a group of volunteers that answered to advertisements in the papers. Each subject received composition in a quantity that lasts for 2 weeks.

Three criteria, Redness, Scale and Itch, were evaluated by the dermatologist on a scale 1 to 4, right before the treatment, immediately at the end of the two weeks treatment and a week after the treatment ended. The same parameters were evaluated "subjectively" by the subjects on a scale of 1 to 10 at the same times.

The results of the experiment were as follows:

According to the numerical graded report of all the subjects, the two-week treatment improved the state of the skin according to all three criteria. In most cases the improvement was clear and significant.

According to the subjects numerical evaluation there was an improvement of 30% ($p<0.08$) in Redness immediately after the treatment ended. A week later an improvement of 45% with $p<0.02$ was reported.

According to the dermatologist numerical evaluation there was an improvement of 38% ($p<0.008$) after 2 weeks of treatment and of 45% ($p<0.005$) a week after the treatment was stopped.

According to the subjects evaluation there was a significant improvement of 25% in Scale ($p<0.09$). A week later an average (insignificant) improvement of 28% was still found ($p=0.16$).

According to the dermatologist evaluation of Scale, there was an average improvement of 25% ($p=0.2$). A week later the improvement still increased and reached an average ($p=13$) improvement of 34%.

The subjects also reported an improvement in Itch but the results had no statistical significance. A week after the treatment ended the improvement still increased and reached an average level of 28% (but still with no statistical significance). Since the values reported for this criterion were low all along the experiment, they are uncertain and probably irrelevant.

The results of experiment 2 are summarized in Table 2.

TABLE 2

Effect of the composition of the present invention on facial Seborrehic Dermatitis (15 subjects)

| Criterion | | Improvement after 2 weeks of treatment | Improvement a week after the treatment ends |
|---|---|---|---|
| REDNESS | Patient evaluation | 30% $p \leq 0.08$ | 45% $p \leq 0.02$ |
|  | Physician evaluation | 38% $p = 0.008$ | 45% $p = 0.005$ |
| SCALE | Patient evaluation | 25% $p \leq 0.09$ | 28% $p = 0.16$ |
|  | Physician evaluation | 25% $p = 0.2$ | 34% $p = 0.13$ |

Experiment 3: The efficiency of a preferred embodiment of the present invention for the treatment of Xerosis.

In a comparative study, the efficiency of a preferred embodiment of the present invention was tested for the treatment of xerosis.

A group of 16 people, suffering from various degrees of xerosis in their lower thighs., were selected by an expert dermatologist, from a group of volunteers that answered to advertisements in the papers. Each subject received composition in a quantity that lasted for 2 weeks.

Two criteria, Dryness and Itch, were evaluated by the subjects on a scale of 1 to 10.

Four criteria, Scale, Cracks, Roughness and Redness, were evaluated by the dermatologist on a scale 1 to 4.

The skin humidity was measured by corneometer CM 820 of Courage and Khazaka.

The evaluations and tests were performed before the treatment, immediately at the end of the two weeks treatment and a week after the treatment ended.

The results of the test were as follows:

A statistical analysis of the results showed clearly that the condition of the subjects improved significantly according to most criteria.

According to the subjects' numerical evaluation, a significant improvement of about 50% ($p<0.01$) in both criteria, Dryness and Itch, was reported. A week after the treatment ended, there was still a significant improvement in both criteria (23% in Dryness, $p<0.02$; 43% for Itch, $p<0.05$).

According to the physician numerical evaluation, the most significant improvement was found in Scale (80%). A week after the treatment there was still an improvement of 57% ($p<0.001$).

A significant improvement was found also for Cracks (83%, $p<0.03$). A week later an average improvement of 66% with $p<0.1$ was found.

In Roughness a clear improvement of 45% ($p<0.01$) was found at the end of the treatment. A week later there was still an improvement but with no statistical significance ($p<0.5$).

The Redness criterion is irrelevant in this case, because it was given very low values even before the treatment.

The corneometer results showed 15% improvement in skin humidity with $p<0.051$.

The results of experiment 3 are summarized in Table 3.

TABLE 3

Effect of the composition of the present invention on Xerosis (16 subjects)

| CRITERIA | | Improvement after 2 weeks of treatment | Improvement a week after the treatment ends |
|---|---|---|---|
| DRYNESS | Patients evaluation | 50% $p \leq 0.01$ | 23% $p \leq 0.02$ |
| ITCH | Patients evaluation | 50% $p \leq 0.01$ | 43% $p \leq 0.05$ |
| SCALE | Physician evaluation | 80% | 57% $p \leq 0.0001$ |
| CRACKS | Physician evaluation | 83% $p \leq 0.03$ | 66% $p = 0.1$ |
| ROUGHNESS | Physician evaluation | 45% $p \leq 0.0.01$ | |
| Humidity | Objective estimation | 15% $p \leq 0.051$ | |

What is claimed is:

1. A leave-on cream emulsion, adapted to be applied to human skin and to be left on said skin for a time sufficient to moisturize said skin and for said skin to substantially completely absorb at least an active ingredient in said emulsion, wherein said emulsion comprises said active ingredient comprising about 1–6 wt. % of a Dead Sea Mud suspension and wherein the amount of said active ingredient is sufficient to retain moisture in said skin and is sufficient to ameliorate at least one disorder of said skin.

2. A cream emulsion according to claim 1 further comprising at least one member selected from the group consisting of octyl palmitate, cetearyl alcohol, ceteareth-30, hexadeacanol, glyceryl stearate, glycerin, PEG-40 stearate, zinc oxide, propylene glycol, aloe barbadensis extract, dimethicone, sorbitan tristearate, allantoin, methylparaben, propylparben, vitamin E and bronopol.

3. A cream emulsion according to claim 1 further comprising up to 4 wt % Dead Sea water.

4. A cream emulsion according to claim 1 further comprising a fragrance.

5. A method for the preparation of a leave-on cream emulsion that is adapted to ameliorate at least one skin condition in a human and is adapted to moisturize said skin comprising:
   a) preparing an oil-in-water emulsion with at least one non-ionic emulsifier(s); and
   b) adding about 1–6 wt. % of a Dead Sea Mud suspension to said emulsion.

6. A method according to claim 5 wherein at least one of said non-toxic emulsifiers is selected from the group consisting of ethoxilated sorbitan esters, sorbitan esters, ethoxilated alcohols, or fatty acids, alkyl glycosides, and mono- and di-glycerides.

7. A method of ameliorating at least one skin condition that comprises:
   applying a cream emulsion, comprising about 1 to 6 wt % of a suspension of active ingredient comprising a Dead Sea Mud suspension, to skin suffering from a disorder; and
   leaving said cream emulsion on said skin until at least substantially all of said Dead Sea Mud has been absorbed by the skin and said disorder has been ameliorated.

8. The method as claimed in claim 7 wherein said skin disorder is at least one member selected from the group consisting of psoriasis, saborrehic dermatitis, xerosis, attopic dermatitas, eczema, diaper rash, skin burns of stage one and sensitive skin.

9. The method as claimed in claim 7 wherein said leave on cream further comprises at least one member selected from the group consisting of octyl palmitate, cetearyl alcohol, ceteareth-30, hexadeacanol, glyceryl stearate, glycerin, PEG-40 stearate, zinc oxide, propylene glycol, aloe barbadensis extract, dimethicone, sorbitan tristearate, allantoin, methylparaben, propylparben, vitamin E and bronopol.

10. The method as claimed in claim 7 wherein said leave on cream further comprises at least about 4 wt % of Dead Sea water.

11. A method of moisturizing skin that comprises:
    applying a cream emulsion, comprising about 1 to 6 wt % of a suspension of active ingredient, comprising a Dead Sea Mud suspension, to skin in need of moisturizing; and
    leaving said cream emulsion on said skin until at least substantially all of said Dead Sea Mud has been absorbed by the skin and said skin has been moisturized.

12. The method as claimed in claim 11 wherein said leave on cream further comprises at least one member selected from the group consisting of octyl palmitate, cetearyl alcohol, ceteareth-30, hexadeacanol, glyceryl stearate, glycerin, PEG-40 stearate, zinc oxide, propylene glycol, aloe barbadensis extract, dimethicone, sorbitan tristearate, allantoin, methylparaben, propylparben, vitamin E and bronopol.

13. The method as claimed in claim 11 wherein said leave on cream further comprises at least about 4 wt % of Dead Sea water.

* * * * *